(12) United States Patent
Salazar et al.

(10) Patent No.: US 8,467,860 B2
(45) Date of Patent: Jun. 18, 2013

(54) PORTABLE SYSTEM AND METHOD FOR MONITORING OF A HEART AND OTHER BODY FUNCTIONS

(76) Inventors: Alexandria Salazar, Mission, TX (US); Rosina Zollino, San Antonio, TX (US)

( * ) Notice: Subject to any disclaimer, the term of this patent is extended or adjusted under 35 U.S.C. 154(b) by 354 days.

(21) Appl. No.: 12/320,151

(22) Filed: Jan. 20, 2009

(65) Prior Publication Data

US 2010/0185062 A1 Jul. 22, 2010

(51) Int. Cl.
*A61B 5/0402* (2006.01)

(52) U.S. Cl.
USPC ........... 600/509; 600/301; 600/508; 600/513; 600/515; 600/522; 600/523

(58) Field of Classification Search
USPC .......... 600/301, 508–509, 513, 515, 522–523
See application file for complete search history.

(56) References Cited

U.S. PATENT DOCUMENTS 7,277,752 B2 * 10/2007 Matos ............................... 607/5
2007/0276270 A1 * 11/2007 Tran .............................. 600/508

\* cited by examiner

*Primary Examiner* — Deborah Malamud

(57) ABSTRACT

Portable systems and methods for continuous and discontinuous monitoring of a user's heart activity, for obtaining a complete, up to twelve-lead electrocardiogram reading are disclosed. A plurality of wearable wired or wireless sensors obtain raw electrocardiogram data from the user. The raw electrocardiogram data is transmitted to data storage media, which include computer instructions for converting the raw data to a complete, up to twelve-lead electrocardiogram reading. The computer instructions can compare the electrocardiogram to one or more predetermined threshold parameters and/or medical standards. The results of the comparison, the electrocardiogram, the parameters, the raw data, the user's location, or combinations thereof, can be transmitted to one or more destinations, which can include medical facilities, insurance providers, emergency responders, and/or family physicians or specialists. The system is thereby usable both for transmitting alerts during emergency situations, and for routine monitoring and diagnosis.

5 Claims, 2 Drawing Sheets

PORTABLE SYSTEM AND METHOD FOR MONITORING OF A HEART AND OTHER BODY FUNCTIONS

FIELD

The present embodiments relate generally to portable, wearable systems and methods for continuous and/or discontinuous monitoring of a user's heart activity, usable for medical evaluation, health awareness, emergency response, and other related purposes. The portable nature of the present embodiments can include use of heart monitoring software coupled with other portable devices, such as cellular (smart) telephones, handheld computer devices, home computers, or similar devices. The present embodiments can be wirelessly networked to enable continuous monitoring and continuously available output to any medium, including hard copy, digital or graphical display, and/or raw data.

BACKGROUND

Conventional medical equipment for obtaining an electrocardiogram reading from an individual obtains up to twelve leads, typically obtained using ten wired electrodes, placed at precise locations on the individual's body, to obtain measurements used to construct the electrocardiogram. Such equipment has not been suitable for continuous monitoring of the individual, as the equipment is not readily portable, and movement of the individual can interfere with the precise placement of one or more of the leads and the accuracy of the readings obtained.

Attempts have been made to create portable means for obtaining electrocardiogram readings, specifically useful for monitoring individuals with potential heart conditions outside of a medical facility. However, these portable devices are typically limited to two or three sensors, which measure heart rate, rhythm, and similar conditions, and construct an electrocardiogram waveform using artificial algorithmic modeling processes. Electrocardiograms obtained in this matter have not been as accurate nor as complete as a twelve-lead electrocardiogram, obtained without use of modeling algorithms.

A twelve-lead electrocardiogram is specifically intended for use as a diagnostic measurement. Electrocardiograms obtained using fewer leads do not obtain QRS-ST-T waveforms with complete accuracy and are typically useful only for determining cardiac rate and rhythm.

Attempts to obtain twelve-lead electrocardiograms using portable means have included "halter monitors" and similar devices, which are used to obtain periodic, intermittent readings over a period ranging from twenty-four to seventy-two hours via wired electrodes, which transmit these readings to a portable recorder. After use, the entire monitor and recorder are typically returned to a physician's office, where the recorded readings can be processed for analysis. Though more accurate than other portable measuring devices, halter monitors are unsuitable for continuous periods of monitoring, especially when it is desirable for a user's mobility to remain unrestricted.

A need exists for a portable heart monitoring system usable to continuously monitor the heart activity of a user to obtain a complete, twelve-lead electrocardiogram reading, through use of wearable electrodes, such as electrodes integrated with one or more pieces of clothing capable of wireless communication. A portable system able to continuously obtain a complete and accurate, twelve-lead electrocardiogram reading would be of significant benefit to individuals having suspected and/or potential heart conditions, which require that the individual be monitored continuously for a lengthy period of time to diagnose the presence or absence of such conditions. Further, a portable system can incorporate the functionality and wireless capabilities of other portable devices, such as cellular (smart) telephones, handheld computers, home computers, or similar devices.

A further need exists for a portable heart monitoring system usable to continuously or periodically monitor a mobile user, such as during athletic events and other instances of physical activity, that can be accessible at any time to obtain the measured data in a variety of output formats.

A need also exists for a portable heart monitoring system that can coordinate data between a centralized database, medical facilities, physicians, insurance providers, and/or other similar individuals and organizations for streamlining the diagnosis, care, and treatment of an individual.

Additionally, a need exists for a portable heart monitoring system usable to detect a heart attack or similar emergency and trigger a response by recognizing a potential emergency condition that exceeds a predetermined safe threshold, and automatically and wirelessly contacting appropriate medical, insurance, and/or emergency response personnel for responding to the user at a specific location.

The present embodiments meet these needs.

SUMMARY

The present embodiments relate generally to a portable system for continuous monitoring of a user's heart activity, usable to obtain a complete, up to twelve-lead electrocardiogram reading. The portable heart monitoring system can be used for medical diagnosis and health monitoring during discrete, individual athletic events or times when aerobic exercise is undertaken, as well as during times of rest. The system is also usable for continuous monitoring of a user's heart activity throughout a selected time period, which can be a brief span of minutes or hours, or a lengthy span of several weeks or months.

In an embodiment, the portable system can be coupled with other portable electronic devices, such as cellular (smart) telephones, handheld computers, home computers, or similar devices. For example, software can be incorporated into a cellular telephone to enable the telephone to monitor and/or process data relating to a wearer's heart activity, and to wirelessly transmit this data, as needed, using existing cellular networks. Use of an existing cellular telephone and/or handheld computer enhances the portability of the present system by enabling a wearer to obtain the benefits of continuous heart monitoring without requiring the user to carry additional processing or monitoring equipment. Further, use of a portable processor eliminates the need for bulky and expensive medical monitoring and processing equipment, while simultaneously providing the user with the conventional telephone, e-mail, web browsing, Global Positioning System, text messaging, and music storage and playback capabilities of a typical portable (smart) telephone or computer.

The system includes a plurality of wearable sensors for continuously obtaining raw electrocardiogram data from a user. Any number of sensors, such as ten or fewer sensors, can be used to obtain up to the twelve leads necessary to produce a complete electrocardiogram. It should be noted that specialized sensors or groups of sensors usable to obtain multiple leads, or specialized techniques for acquiring an electrocardiogram, could enable a twelve-lead electrocardiogram reading to be obtained using fewer than ten sensors. In an embodiment, the present system can include from three to six wearable sensors, or more.

The sensors should be attachable to the user in a manner that resists displacement or detachment as the user moves, and that will not cause discomfort or injury to the user through long-term use, such as through use of various adhesives or medical tapes. In an embodiment, one or more of the sensors can be integrated with an article of clothing, such as a close-fitting shirt, a pair of running shorts, bands, belts, braces, or similar articles of clothing or underclothing sufficiently fitted to maintain the sensors in positions usable to obtain the electrocardiogram reading. The sensors can thereby be made wearable, allowing a user's heart to be monitored continuously, without restricting the user to a medical facility and without substantially restricting the user's mobility or activities.

The sensors can be in wireless or wired communication with one or more portable data storage media worn or carried by the user, or in wireless communication with one or more data storage media remote from the user. Any worn or carried data storage media proximate to the user can be in wireless communication with one or more remote data storage media or other destinations. Use of a cellular (smart) telephone, handheld or home computer, or other similar device can facilitate wireless communication between the present system and remote data storage media. Additionally or alternatively, data storage media integral with a portable wireless device can be used for recording data from the sensors. Use of a wireless network can enable data obtained using the sensors to be processed at any time, and output from the monitoring process to be obtained at any time, from any location. Use of a smart phone and/or a computer device in conjunction with the sensors can enable in-the-spot, instantaneous processing of data at any time, and can enable a complete electrocardiogram reading to be displayed and/or transmitted using the smart phone display or computer screen.

The system can also be fitted with or otherwise in communication with a locating device, such as a global positioning chip, transmitter, receiver, or similar device, used to determine the location of the user. In an embodiment, the locating device can be integral with a portable wireless device carried by the user. In an embodiment, global positioning software, or similar computer instructions, can be used to display maps, textual and/or visual directions, or other information based on data obtained from the locating device using a display device in communication with the locating device.

Data storage media in direct or wireless communication with the sensors and/or the locating device is used to receive the raw electrocardiogram data from the sensors. Software in the data storage media can be used to instruct a processor to convert the raw electrocardiogram data to a complete, twelve-lead electrocardiogram waveform for analysis and interpretation by a medical professional, including a medical technologist and/or technician, without use of artificial modeling algorithms or similar extrapolations.

Stored within the data storage media can be one or more predetermined threshold parameters relating to the electrocardiogram. The threshold parameters can be general, or specific to a user, depending on any known or suspected heart conditions or other medical conditions of the user. Customized threshold parameters specific to a patient can be provided and/or set by a physician, a technician, or another medical provider, technologist, and/or technician. Usable software can include pre-defined fields for patient data entry, customized fields specific to certain providers or patients, or combinations thereof.

The software can be used to compare the electrocardiogram reading to the threshold parameters, then initiate transmission of the results of the comparison, the electrocardiogram, the threshold parameters, the user's location, or combinations thereof, to an appropriate destination, such as a centralized database, an insurance provider, a medical facility, a medical provider, an emergency response facility, or other similar facilities or personnel. Transmissions could also be provided to the user and/or a designated third party, such as a family member or friend of the user.

The transmission output can include any format, including a graphical display and/or hard copy. For example, a hard copy of a produced electrocardiogram waveform could be generated through a facsimile transmission from a user's wireless telephone or computer. While conventional equipment for obtaining and producing an electrocardiogram is complex, requiring specialized training to operate, the present system can allow a simple operation, such as the pressing of a button by the user and/or a remote viewer, to initiate acquisition, storage, and/or printing/display of a complete electrocardiogram.

The software can also provide an alert, such as an audible or visual alarm, a tactile response, such as a vibration, and/or a message to the user, one or more destinations, one or more designated third parties, or combinations thereof, when one or more of the predetermined threshold parameters are met or exceeded.

The alert can also include a textual message containing at least a portion of the electrocardiogram reading, one or more threshold parameters, the location of the user, other similar information, or combinations thereof.

The present system is thereby usable to streamline an emergency response, medical treatment, and/or insurance processing during an emergency situation. Further, in absence of an emergency situation, the present system is usable to efficiently store, process, and maintain electrocardiogram-related data regarding a user for medical review and diagnosis, analysis, and processing.

In an embodiment, to protect the user's privacy, the present system can be configured to determine and transmit the location of the user only during an emergency situation, as part of an alert indicating an electrocardiogram reading that meets or exceeds one or more of the predetermined threshold parameters in a manner that necessitates an emergency response.

While the present system is especially useful for measuring heart activity and forming a complete, up to twelve-lead electrocardiogram, in an embodiment, the present system can also be configured to measure a user's heart rate, oxygen saturation level, breath rate, temperature, other similar medical information, or combinations thereof. Any combination of any measured information regarding the user can be compared to relevant predetermined threshold parameters in the data storage. Further, any combination of measured information can be transmitted to any combination of insurance-related, medical, and/or emergency facilities, personnel, or databases, in emergency situations or non-emergency situations.

The present embodiments also relate to a method for continuously or periodically monitoring an individual's heart that includes obtaining raw electrocardiogram data from a user, as described previously, using a plurality of portable sensors.

The raw electrocardiogram data is converted to a complete electrocardiogram, which is compared to one or more predetermined threshold parameters and/or medical standards. The raw data, the complete electrocardiogram, the threshold parameters, the comparison results, and/or the user's location can be transmitted to selected destinations for analysis, evaluation, and/or action. The transmission can be coupled with an alert if the electrocardiogram exceeds meets or one or more threshold parameters. The location of the user can also be obtained and transmitted to the destination if it is determined that the electrocardiogram meets or exceeds one or more of the threshold parameters.

In addition to monitoring and transmitting data relating to the electrocardiogram, the method can include obtaining a heart rate, oxygen saturation level, breath rate, temperature, or other similar measurements, comparing these measurements to threshold parameters, and/or transmitting these measurements to selected destinations.

The present systems and methods thereby enable continuous monitoring of an individual's heart activity and obtain a complete, up to twelve-lead electrocardiogram reading, which can be selectively transmitted to various insurance-related, medical, and/or emergency facilities to maximize the efficiency of medical diagnosis and treatment, insurance processing, and emergency response.

Further, the continuous monitoring ability of the present systems and methods enable heart attacks and other potentially emergent heart conditions to be immediately detected, and an instantaneous alert to be provided to the user and/or relevant medical and emergency response facilities, coupled with the complete electrocardiogram, which enables an appropriate diagnosis and treatment to be formulated as rapidly as possible, even prior to the user's arrival at a medical facility, when time is of the essence and such efficiency can prevent a fatality.

Through use of wirelessly networked portable devices, the present systems and methods enable seamless, continuous, and instantaneous access to electrocardiogram waveforms and related data and information. Further, through wireless communication, instant assistance can be obtained regarding an emergency situation or a need for assistance utilizing or operating the present system. For example, the present system can include a user-accessible help button, online or networked instructions, or similar information and/or features.

The present systems and methods transform the typically complex steps involved in the production of an electrocardiogram into a simple and automated process, with customizable and configurable measurements, interpretation, and memory requirements, and selectable report and/or output formats.

BRIEF DESCRIPTION OF THE DRAWINGS

In the detailed description of the embodiments presented below, reference is made to the accompanying drawings, in which.

The present embodiments are detailed below with reference to the listed Figures.

DETAILED DESCRIPTION OF THE EMBODIMENTS

Before explaining the present embodiments in detail, it is to be understood that the embodiments are not limited to the particular descriptions and that the embodiments can be practiced or carried out in various ways.

Figure 1B:
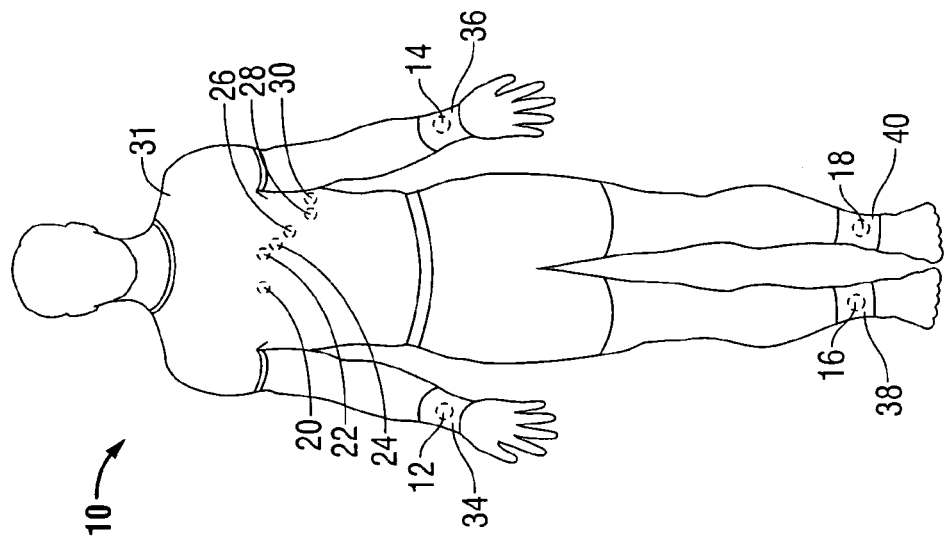
FIG. 1B depicts a diagram of an alternate embodiment an arrangement of wearable sensors.
Figure 1A:
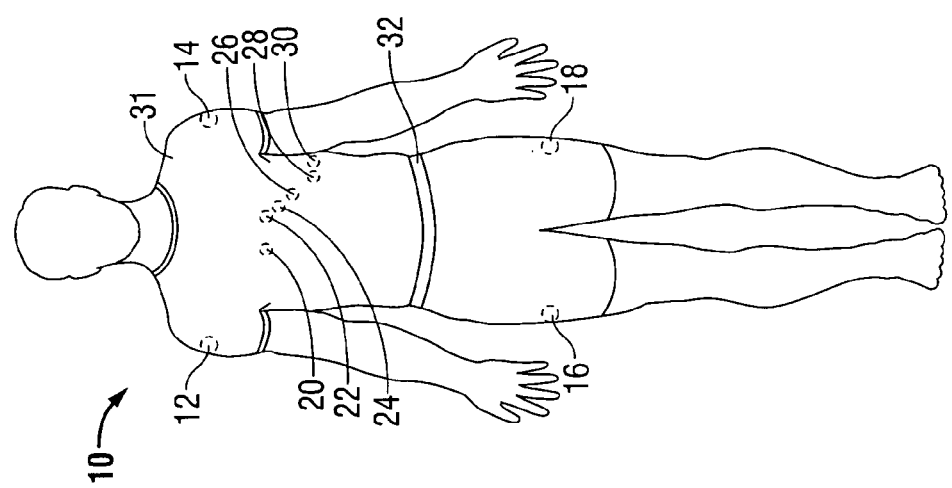
FIG. 1A depicts a diagram of an embodiment of an arrangement of wearable sensors usable with the present system.

Referring now to FIG. 1A, a diagram of an exemplary arrangement of sensors usable with the present system is shown.

FIG. 1 depicts a user (10) having a plurality of wearable sensors disposed thereon in an arrangement usable to obtain a twelve-lead electrocardiogram. For purposes of this application, a twelve-lead electrocardiogram is considered to be a measurement of a heart's electrical signal, depicted using accurate P-QRS-T waveforms obtained by measuring the heart from a variety of angles, which constitute the twelve leads. A twelve-lead electrocardiogram is also usable to determine P-R and Q-T intervals and ST segments.

In an embodiment, a diagnostic-grade frequency response for an electrocardiogram can range from 0.05 hertz to 150 hertz, while for monitor quality, the frequency response can range from 0.5 hertz to 20 to 50 hertz.

Typically, six of the twelve leads are obtained using four limb sensors. FIG. 1A depicts a right arm sensor (12) and a left arm sensor (14), disposed at the user's right and left shoulders, respectively, proximate to the collarbone. A right leg sensor (16) and a left leg sensor (18) are shown disposed at the user's right and left legs, respectively, proximate to the hips.

While typically, arm and leg sensors can be positioned at the wrists and ankles to obtain a twelve-lead electrocardiogram, it is also possible to obtain an accurate electrocardiogram through placement of sensors at differing locations along the limbs, as long as the limb sensors are not placed in contact with the torso.

The arm and leg sensors (12, 14, 16, 18) obtain Leads I, II, and III not shown, which are bipolar leads, each having negative and positive electrodes. Once the data obtained from the sensors (12, 14, 16, 18) is processed, the electrocardiogram is produced using the voltage differences between the active electrodes of each of Leads I, II, and III. Lead I is typically determined through the difference in the readings obtained by the left arm sensor (14) and the right arm sensor (12). Lead II is typically determined through the difference in readings obtained by the left leg sensor (18) and the left arm sensor (14). Lead III is typically determined through the difference in the readings obtained by the left leg sensor (18) and the right arm sensor (12).

The arm and leg sensors (12, 14, 16, 18) can also be used to obtain the augmented voltage right, left, and foot (aVR, aVL, aVF) leads, which are negative unipolar leads. The aVR lead is determined by using the right arm sensor (12) as a positive electrode, and the other limb sensors (14, 16, 18) as negative electrodes. The aVL lead is determined by using the left arm sensor (14) as a positive electrode, and the other limb sensors (12, 16, 18) as negative electrodes. The aVF lead is determined by using left leg sensor (18) as a positive electrode, and the other limb sensors (12, 14, 16) as negative electrodes.

Once data obtained from the sensors (12, 14, 16, 18) is processed, the electrocardiogram is produced using voltage differences between the aVR lead and the right arm sensor (12), the aVL lead and the left arm sensor (14), and the aVF lead and the left leg sensor (18).

The remaining six leads, termed V1 through V6 not shown, can be obtained using six precordial sensors secured to the user's chest. A first precordial sensor (20) is shown positioned to the right of the user's sternum, over the forth intercostal space. A second precordial sensor (22) is shown positioned approximately horizontally even with the first precordial sensor (20), to the left of the user's sternum, over the forth intercostal space.

A fourth precordial sensor (26) is shown positioned below and to the right of the second precordial sensor (22) over the fifth intercostal space at the user's midclavicular line. A third precordial sensor (24) is positioned directly between the second and fourth precordial sensors (22, 26), at the midpoint.

A fifth precordial sensor (28) is shown positioned approximately horizontally even with the fourth precordial sensor (26) at the left anterior axillary line. A sixth precordial sensor (30) is shown positioned approximately horizontally even with the fourth and fifth precordial sensors (26, 28), at the left midaxillary line directly underneath the user's left arm.

Each of the precordial sensors (20, 22, 24, 26, 28, 30) can obtain one of Leads V1 through V6, which are positive unipolar leads. Leads V1 and V2 observe the right side of the heart, facing the user's back. Leads V3 and V4 observe the interventricular septum, facing the user's back. Leads V5 and V6 observe the left side of the heart, facing the user's back.

In combination with the six leads obtained using the arm and leg sensors (12, 14, 16, 18), a complete, twelve-lead electrocardiogram can be produced.

Each of the sensors can include a battery and/or capacitor for providing power to obtain readings from the user (10) and to wirelessly transmit the readings. In an embodiment, one or more of the sensors can be in wired communication with a portable power source carried by the user (10).

The arm sensors (12, 14) and each of the precordial sensors (20, 22, 24, 26, 28, 30) are shown integrated with a shirt (31) worn by the user (10). The shirt (31) can be sufficiently tight-fitting and made from a material having sufficient friction against the body to prevent movement of any of the integrated sensors. While FIG. 1A depicts a shirt (31), other articles of clothing that cover appropriate areas of the user's body could also be used to secure the sensors, such as a halter-top or undergarment. Also, one or more bands or strips having the sensors integrated within can be strapped, draped, or otherwise fastened or secured to the user's body, to be worn beneath clothing.

The two leg sensors (16, 18) are shown integrated with a pair of shorts (32) worn by the user (10). The shorts (32) can be sufficiently tight-fitting and made from a material having sufficient friction against the body to prevent movement of any of the integrated sensors, such as running or biking shorts, undergarment shorts, or similar types of clothing. While FIG. 1A depicts shorts (32), other types of clothing for the lower body, such as pants, could also be used. Additionally, one or more bands having the sensors integrated within can be strapped, draped, or otherwise secured to the user's body, to be worn beneath clothing.

Referring now to FIG. 1B, an alternate arrangement for the plurality of wearable sensors is shown.

The user (10) is shown wearing a shirt (31) with which each of the precordial sensors (20, 22, 24, 26, 28, 30) are integrated, as described previously.

The right arm sensor (12) is shown integrated with a right wristband (34), the left arm sensor (14) is shown integrated with a left wristband (36), the right leg sensor (16) is shown integrated with a right ankle band (38), and the left leg sensor (18) is shown integrated with a left ankle band (40).

Each of the wrist and ankle bands (34, 36, 38, 40) can be sufficiently tight-fitting and made from a material having sufficient friction against the body to prevent movement of any of the integrated sensors.

It should be noted that the arrangements of clothing depicted in FIGS. 1A and 1B are non-limiting, exemplary embodiments, and that any arrangement of clothing, undergarments, bands, straps, patches, or similar objects can be used to maintain the position of each of the sensors on the user's body. For example, the arrangement of sensors shown in FIG. 1B could be obtained by integrating the limb sensors into the ankles of a pair of pants and into the ends of the sleeves of a long-sleeved shirt.

Figure 2:
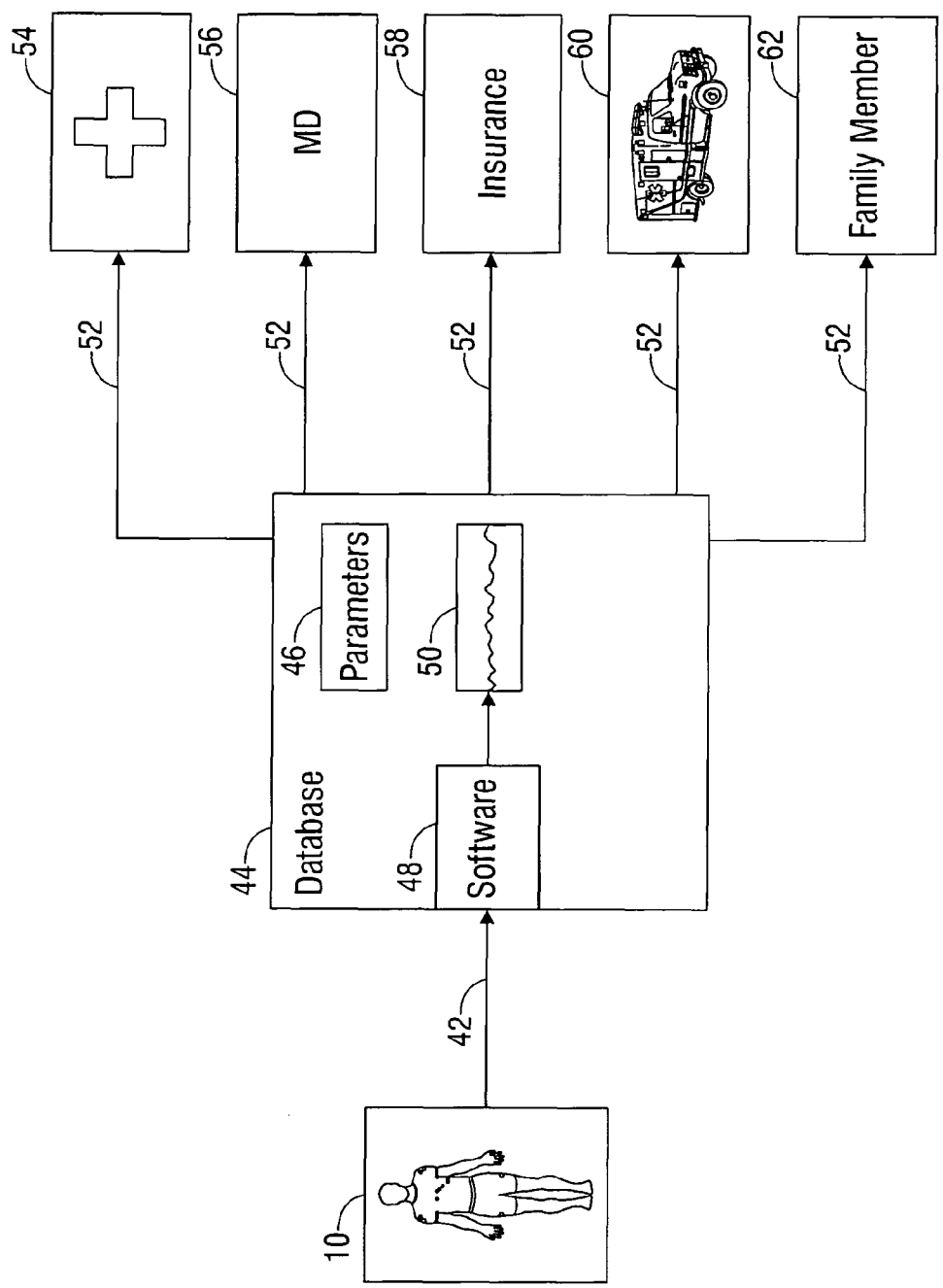
FIG. 2 depicts a diagram of an embodiment of the present system.

Referring now to FIG. 2, a diagram of an embodiment of the present system is shown.

The user (10) of FIGS. 1A and 1B is depicted, having a plurality of wearable sensors disposed thereon for obtaining raw electrocardiogram data, and in an embodiment, the current location of the user (10). The raw electrocardiogram data (42) and/or the location of the user (10) is shown being wirelessly transmitted from the user (10) to a centralized database (44), which can include an integral or remote processor.

The centralized database (44) can be stored within one or more data storage media worn or carried by the user (10), or stored within one or more data storage media remote from the user (10). In an embodiment, the centralized database (44) can be integral with a portable device or other processing device, which can include a cellular (smart) telephone, a handheld computer, a home computer, or a similar device able to store and process data.

Software (48), which can be stored within the same data storage medium containing the database (44), or a different data storage medium in communication with the database (44), is used to convert the raw electrocardiogram data (42) to a complete electrocardiogram (50). The software (48) can perform sensor checks to ensure the integrity of each lead obtained by the sensors and provide a simultaneous, real-time review of all sensor paths. If a device having a display is utilized to process the raw electrocardiogram data (42), the complete electrocardiogram (50) and/or other related information can be displayed, eliminating the need for a separate monitoring and display device and any training required to utilize the separate device.

The software (48) can then compare the complete electrocardiogram (50) to one or more threshold parameters (46), which can be stored within the same data storage medium containing the database (44), the software (48), or a different data storage medium.

The complete electrocardiogram (50), the parameters (46), the raw electrocardiogram data (42), the user's location, and/or the results of the comparison performed using the software (48) can be used to form a transmission (52). The transmission (52) can be individually or simultaneously sent to one or more destinations.

FIG. 2 depicts the transmission (52) being sent to a hospital (54), a physician (56), an insurance provider (58), an emergency response facility (60), and a family member (62). The transmission (52) can include various types of output, including visual output on a monitor screen or other display device, hard copy via a facsimile or printer, or data recorded and stored for future analysis.

It should be noted that the arrangement of data storage and destinations depicted by FIG. 2 is exemplary, and that various other configurations and arrangements are also possible. For example, the centralized database (44) could be omitted, and the raw electrocardiogram data (42) could be transmitted directly to any of the destinations (54, 56, 58, 60, 62), where software (48) could be used to convert the data (42) to the complete electrocardiogram (50).

The present systems and methods thereby enable continuous and accurate monitoring of a user's heart, to obtain a complete, up to twelve-lead electrocardiogram, while providing for the incorporation and use of portable wireless devices to eliminate excess equipment and facilitate the constant availability of the obtained information. The present systems and methods minimize obsolescence and maximize information sharing, enabling real-time monitoring and detection of medical conditions, including emergency situations, coupled with an easily acquired, on-line help connection and a variety of usable output formats. Further, the present systems and methods are adaptable to meet specific needs relating to any patient, physician, insurance provider, and/or medical facility, while ensuring the integrity and privacy of the data obtained.

While these embodiments have been described with emphasis on the embodiments, it should be understood that within the scope of the appended claims, the embodiments might be practiced other than as specifically described herein.

What is claimed is:

1. A method for continuous monitoring of heart activity of a user, the method comprising the steps of:
   providing at least six sensors to limbs and a torso of a user, wherein said at least six sensors are configured for portability to enable a continuous period of diagnostic monitoring of the user sufficient to form a medical diagnosis;
   obtaining raw electrocardiogram data sufficient to determine a complete diagnostic twelve-lead electrocardiogram reading from the user using said at least six sensors configured for continuous monitoring of the user;
   maintaining said at least six sensors in association with the user for a period of diagnostic monitoring sufficient to form the medical diagnosis;
   converting the raw electrocardiogram data to a complete diagnostic twelve-lead electrocardiogram reading suitable for formulating a medical diagnosis;
   comparing the complete diagnostic twelve-lead electrocardiogram reading to at least one predetermined threshold electrocardiogram parameter to form a comparison;
   transmitting the complete diagnostic twelve-lead electrocardiogram reading to at least one destination;
   formulating the medical diagnosis of the user at said at least one destination using the complete diagnostic twelve-lead electrocardiogram reading; and
   wherein the continuous monitoring is done while performing routine mobile activities.

2. The method of claim 1, further comprising the step of:
   determining a location of the user if the complete diagnostic twelve-lead electrocardiogram reading exceeds said at least one predetermined threshold electrocardiogram parameter and transmitting the location to said at least one destination.

3. The method of claim 1, further comprising the step of:
   providing an alert to the user, said at least one destination, or combinations thereof, if the complete diagnostic twelve-lead electrocardiogram reading exceeds said at least one predetermined threshold electrocardiogram parameter.

4. The method of claim 1, further comprising the steps of:
   measuring a heart rate of the user, an oxygen saturation level of the user, a breath rate of the user, a temperature of the user, or combinations thereof; and
   transmitting the heart rate, the oxygen saturation level, the breath rate, the temperature, or combinations thereof, to said at least one destination.

5. The method of claim 4, further comprising the steps of:
   comparing the heart rate, the oxygen saturation level, the breath rate, the temperature, or combinations thereof, to at least one predetermined threshold parameter; and
   providing the alert to the user, said at least one destination, or combinations thereof, if the heart rate, the oxygen saturation level, the breath rate, the temperature, or combinations thereof, exceeds said at least one predetermined threshold parameter.

* * * * *